US012121685B2

(12) United States Patent
Amery

(10) Patent No.: US 12,121,685 B2
(45) Date of Patent: Oct. 22, 2024

(54) ELECTRONIC VALVE READER HAVING ORIENTATION SENSING MECHANISM

(71) Applicant: Medtronic Xomed, Inc., Jacksonville, FL (US)

(72) Inventor: Drew Amery, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

(21) Appl. No.: 18/345,265

(22) Filed: Jun. 30, 2023

(65) Prior Publication Data

US 2023/0338716 A1   Oct. 26, 2023

Related U.S. Application Data

(63) Continuation of application No. 17/464,241, filed on Sep. 1, 2021, now Pat. No. 11,712,546, which is a
(Continued)

(51) Int. Cl.
*A61M 27/00* (2006.01)
*G01D 5/12* (2006.01)
*G01D 7/00* (2006.01)

(52) U.S. Cl.
CPC ............ *A61M 27/006* (2013.01); *G01D 5/12* (2013.01); *G01D 7/00* (2013.01); *A61M 2205/18* (2013.01);
(Continued)

(58) Field of Classification Search
CPC ............ A61M 27/006; A61M 2205/18; A61M 2205/3327; A61M 2205/50;
(Continued)

(56) References Cited

U.S. PATENT DOCUMENTS 5,637,083 A    6/1997  Bertrand et al.
5,879,297 A    3/1999  Haynor et al.
(Continued)

FOREIGN PATENT DOCUMENTS

CN     107320806 A     11/2017
WO     2015157320 A1   10/2015

OTHER PUBLICATIONS

Korean First Office Action dated Sep. 5, 2022 corresponding to Korean Patent Application No. 10-2019-7003820, corresponding to PCT/US2017/042369.
(Continued)

*Primary Examiner* — Tung X Nguyen
*Assistant Examiner* — Trung Q Nguyen
(74) *Attorney, Agent, or Firm* — Harness, Dickey & Pierce, P.L.C.

(57) ABSTRACT

Magnetic-based electronic valve readers for determining a location and orientation of magnets coupled to implantable medical devices to determine a setting of the device (e.g., setting of a fluid flow control valve of the medical device). The electronic valve readers include an orientation sensing mechanism that is provided and configured to enable the electronic valve reader to: 1) allow for internal offset calculation of an orientation change of the electronic valve reader during a reading process; and/or 2) during the reading process, provide an indication or warning to the clinician that the orientation of the electronic valve reader has changed to an extent at or exceeding a predetermined angular acceptance threshold or window. Systems including the disclosed electronic valve readers and methods of reading a setting of the device are also disclosed.

20 Claims, 10 Drawing Sheets

Related U.S. Application Data continuation of application No. 15/651,489, filed on Jul. 17, 2017, now Pat. No. 11,141,574.

(60) Provisional application No. 62/363,524, filed on Jul. 18, 2016.

(52) U.S. Cl.
CPC ............... *A61M 2205/3317* (2013.01); *A61M 2205/3327* (2013.01); *A61M 2205/50* (2013.01); *A61M 2205/502* (2013.01); *A61M 2205/52* (2013.01)

(58) Field of Classification Search
CPC ........ A61M 2205/502; A61M 2205/52; G01D 5/12; G01D 7/00
USPC ... 324/329–348, 323, 447, 425, 206–207.26, 324/256–259, 600, 637, 639, 658, 200
See application file for complete search history.

(56) References Cited

U.S. PATENT DOCUMENTS

| | | | |
|---|---|---|---|
| 6,129,668 A | | 10/2000 | Haynor et al. |
| 7,334,582 B2 | | 2/2008 | Bertrand et al. |
| 8,622,978 B2 | | 1/2014 | Bertrand et al. |
| 9,569,589 B1 | | 2/2017 | LaBorde |
| 11,141,574 B2 | * | 10/2021 | Amery .................... G01D 5/12 |
| 11,712,546 B2 | * | 8/2023 | Amery ................ A61M 27/006 |
| | | | 324/207.25 |
| 2005/0092335 A1 | * | 5/2005 | Bertrand .................. A61B 5/06 |
| | | | 128/899 |
| 2005/0096579 A1 | | 5/2005 | Bertrand et al. |
| 2008/0221436 A1 | | 9/2008 | Bertrand et al. |
| 2009/0305212 A1 | | 12/2009 | McKenzie et al. |
| 2010/0010338 A1 | | 1/2010 | van Dam et al. |
| 2011/0112460 A1 | * | 5/2011 | Murphy .............. A61M 27/006 |
| | | | 604/9 |
| 2012/0197238 A1 | | 8/2012 | Whitehead et al. |
| 2013/0177455 A1 | | 7/2013 | Kamen et al. |
| 2014/0052047 A1 | | 2/2014 | Wilson |
| 2017/0209056 A1 | | 7/2017 | Browd et al. |
| 2017/0341880 A1 | | 11/2017 | Strobel et al. |
| 2019/0083764 A1 | * | 3/2019 | Boden, Jr. ........... A61M 27/006 |

OTHER PUBLICATIONS

Freescale Semiconductor, Inc. Data Sheet: Technical Data, "3-Axis Digital Angular Rate Gyroscope", FXAS21002C, Rev. 2.1, May 2015 (58 pgs).

Freescale Semiconductor, Inc. Technical Data, "+2g/+4g/+8g Three Axis Low-g Digital Output Accelerometer", Document No. MMA7456L, Rev. 4, Apr. 2009 (35 pgs).

STMicroelectronics—life.augmented, ST's solutions for mobile devices, Dec. 2015 (47 pgs).

A International Search Report and Written Opinion for PCT/US2017/042369 mailed Sep. 22, 2017 (14 pgs).

* cited by examiner

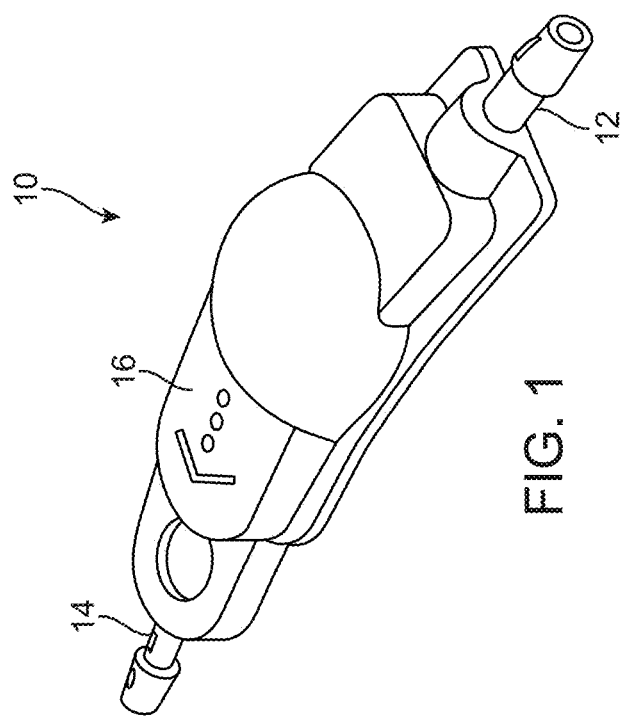
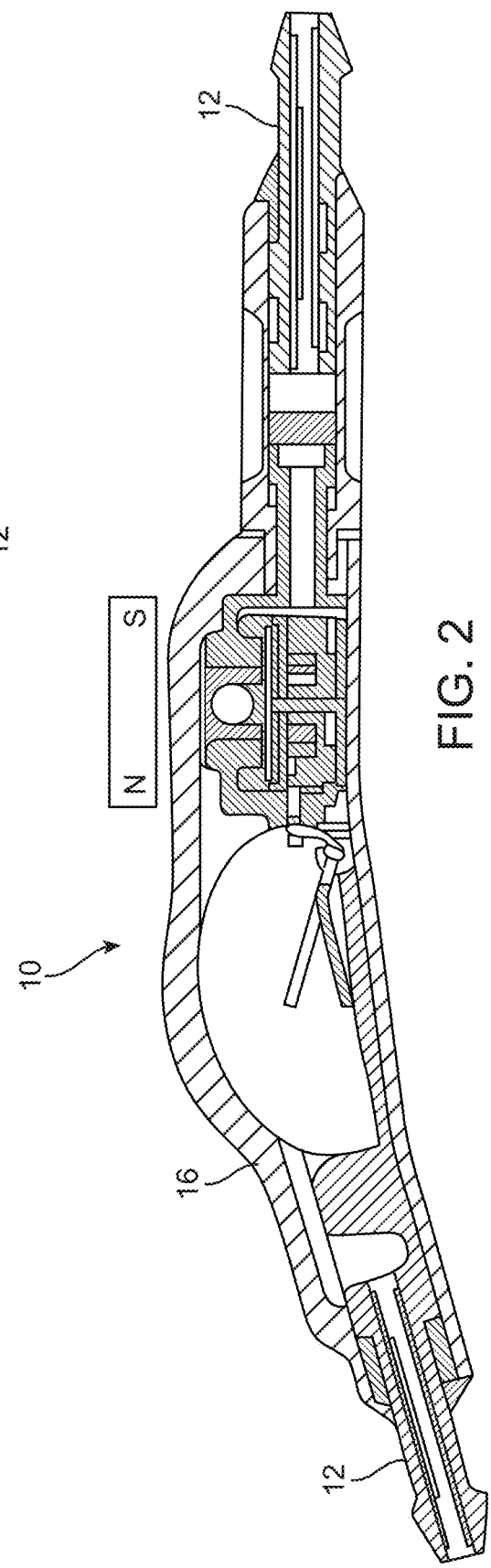

ELECTRONIC VALVE READER HAVING ORIENTATION SENSING MECHANISM

CROSS-REFERENCE TO RELATED APPLICATIONS

This application is a Continuation application of Ser. No. 17/464,241 filed Sep. 1, 2021, entitled, "ELECTRONIC VALVE READER HAVING ORIENTATION SENSING MECHANISM," now allowed, which claims the benefit of the filing date of U.S. application Ser. No. 15/651,489, filed on Jul. 17, 2017, entitled, "ELECTRONIC VALVE READER HAVING ORIENTATION SENSING MECHANISM," issued as U.S. Pat. No. 11,141,574, which claims the benefit of the filing date of U.S. Provisional Patent Application Ser. No. 62/363,524, filed Jul. 18, 2016, entitled "ELECTRONIC VALVE READER HAVING ORIENTATION SENSING MECHANISM," the entire teachings of which are incorporated herein by reference.

BACKGROUND

The present disclosure relates to medical devices and, more particularly, to magnetic-based electronic valve readers.

Magnetic-based indicator tools or valve readers are used to determine a setting of an implantable medical device. The implantable medical device may include a fluid flow control valve that controls the pressure of cerebral spinal fluid (CSF) in a patient's brain. Excessive accumulation of cerebral spinal fluid (CSF), due to hydrocephalus or other causes, manifests itself as increased pressure within the brain. Relieving the CSF pressure is therapeutically beneficial and is usually done by using a fluid flow control valve to drain CSF from ventricles in the brain.

The implantable medical device may include a target in the form of a magnet. The magnet allows a tool set to determine the setting of the medical device and change the setting without removing the subcutaneously implanted device. The tool set typically includes a locator tool to determine the orientation of the medical device, the magnetic-based indicator tool to determine the setting of the implantable medical device with a mechanical compass, and an adjustment tool to change the setting of the medical device by using another magnet. The tool set works by using magnetic coupling between the magnet on the implantable medical device and each of the indicator tool compass and the adjustment tool magnet.

The mechanical compass-based indicator tool relies on an interaction between the magnet on the medical device and the compass that is strong enough to determine the position of the magnet, even through a patient's scalp. The magnet-compass interaction must also be resistant to external magnetic fields, especially from the Earth. The compass will drift toward aligning with the Earth's magnetic field if the pull of the magnet in the implanted medical device is not strong enough. The deflection angle increases as the distance between the magnet and the compass increases, and may lead to inaccurate device setting indications.

Alternatively, magnetic-based indicator tools have been developed to determine the three-dimensional location and orientation of magnetic devices within implanted medical devices, such as medical tubes and catheters. These alternate location systems typically do not relate to the rotatable orientation of magnetic devices that are part of implantable valve devices. An example of such a device is disclosed in U.S. Pat. No. 7,334,582 (Bertrand et al.), the disclosure of which is hereby incorporated by reference.

U.S. Pat. No. 8,622,978 to Bertrand et al. discloses a compass-based indicator for assessing the position of a fluid flow valve within an implanted device. The fluid flow valve described by Bertrand et al. may be used for controlling the flow of cerebral spinal fluid (CSF) in a patient with hydrocephalus. This compass-based indicator is used in combination with an implantable flow control device disclosed within U.S. Pat. No. 5,637,083 to Bertrand et al. U.S. Pat. No. 5,879,297 and U.S. Pat. No. 6,129,668 to Haynor et al. discloses an electronic device to determine the location and orientation of a magnet coupled to an indwelling medical device using a plurality of magnetic sensors. Table 1 below lists documents that disclose devices for determining the location and orientation of magnetic devices within implantable medical devices.

TABLE 1

| Patent Number | Inventors | Title |
| --- | --- | --- |
| U.S. Pat. No. 7,334,582 | Bertrand et al. | Implantable Adjustable Fluid Flow Control Valve |
| U.S. Pat. No. 8,622,978 | Bertrand et al. | Tool for Adjusting an Implantable Adjustable Fluid Flow Control Valve |
| U.S. Pat. No. 5,879,297 | Haynor et al. | System and Method to Determine the Location and Orientation of an Indwelling Medical Device |
| U.S. Pat. No. 6,129,668 | Haynor et al. | System and Method to Determine the Location and Orientation of an Indwelling Medical Device |

All documents listed in Table 1 above are hereby incorporated by reference herein in their respective entireties. The present inventor believes that any of the devices and methods disclosed in the patents of Table 1 may be modified advantageously by using the structures and techniques of the present disclosure.

SUMMARY

The present disclosure is directed to magnetic-based electronic valve readers for determining a location and orientation of magnets (magnetic indicator devices) coupled to implantable medical devices, such as a fluid flow control valve that controls the pressure of cerebral spinal fluid (CSF). The electronic valve reader interacts with the implanted medical device to assess a setting associated with the implantable medical device. The magnetic-based electronic valve reader includes a plurality of magnetic sensor devices (i.e. magnetic field sensors), an orientation sensing mechanism and a processing system that uses data generated from the plurality of magnetic sensor devices to determine a location and orientation of the magnetic indicator device. The magnetic indicator device, being coupled to the fluid flow control valve used to control operation on the implantable medical device, permits the processing system to further determine the setting of the control valve from the location and orientation of the magnetic indicator device.

In certain embodiments, the processing system utilizes digital measurements and information generated from the orientation sensing mechanism to determine the location and orientation of the magnetic indicator device by accounting for changes in three-dimensional (i.e. x-y-z-axis) orientation of the electronic valve reader as the electronic valve reader is positioned proximate the implantable medical device. The orientation sensing mechanism can also, or alternatively, be used to provide digital measurements and information to the processing system, which can be configured to use the digital measurements or information to monitor the orientation of the electronic valve reader and alert the clinician (e.g., visually, audibly, etc.) that the electronic valve reader housing is nearing an undesired or unacceptable variance in or loss of orientation.

The orientation sensing mechanism of the electronic valve readers disclosed herein provide significant advantages as compared to known reading devices. With certain known reading devices, an electronic reader estimates the external magnetic fields to subtract the estimated external magnetic field from the data received to minimize an influence that any external magnetic fields have on the accuracy of the device setting measurement. This process requires the user to substantially maintain x-y-z-axis orientation of the electronic reader, relative to the Earth, between a zero setting (subtraction or taring) operation and application of the electronic valve reader over the implanted medical device. Due to human limitations and the nature of the procedure, maintaining the x-y-z-axis orientation of the electronic reader during use is difficult to achieve and can result in a clinician having to conduct multiple attempts before a reading is obtained. In the disclosed embodiments, the orientation sensing mechanism is provided and configured to enable the electronic valve reader to: 1) allow for internal offset calculation of or accounting for an orientation change of the electronic valve reader; and/or 2) provide an indication or warning to the clinician that the orientation of the electronic valve reader has changed to an extent at or exceeding a predetermined angular acceptance window. To serve as a warning, the angular acceptance window is set to be less than that which would result in a "loss of orientation" error message from the electronic valve reader, thus requiring the clinician to restart the reading process and recalibrate the electronic valve reader. Therefore, disclosed electronic valve readers having the orientation sensing mechanism are easier to use, thus likely reducing procedure times and user frustration.

Additional aspects of the present disclosure are directed to systems comprising an implantable medical device that includes an implantable flow control device, an electronic valve reader, and an adjustment tool. The implantable flow control device includes a magnetic indicator device coupled to a fluid flow control valve. The electronic valve reader includes a plurality of magnetic sensor devices, an orientation sensing mechanism and a processing system that uses data generated from the plurality of magnetic sensor devices to determine a location and orientation of a magnetic indicator device. The magnetic indicator device, being coupled to the control valve used to control operation on an implantable flow control device, permits the processing system to further determine a setting for the control valve from the location and orientation of the magnetic indicator device. In certain embodiments, the orientation sensing mechanism provides information to the processing system that is used in the determination of the location and orientation of the magnetic indicator device. In some embodiments, the processing system is configured to utilize digital measurements and information generated from the orientation sensing mechanism to provide an indication and alert the user, if applicable, that the electronic valve reader is nearing an unacceptable variance or loss of orientation during the reading process.

The present disclosure further includes methods of determining a location and orientation of a magnetic indicator device that comprise placing an electronic valve reader adjacent to an implantable medical device, detecting a magnetic field from a plurality of target magnetic sensor devices, estimating a background magnetic field from a sequence of magnetic field data observed over time by a plurality of background magnetic sensor devices, and indicating a device setting (e.g., control valve setting) of the implantable medical device by the electronic valve reader. The plurality of target magnetic sensor devices and the plurality of background magnetic sensor devices are located a distance apart sufficient to permit the background magnetic field sensor devices to only detect ambient magnetic fields when the target magnetic sensor devices are located near the implanted flow control device. In certain embodiments, the method includes using the orientation sensing mechanism of the electronic valve reader to collect digital measurements regarding the orientation of the electronic valve reader between a zero setting (subtraction or taring) operation and application of the electronic valve reader over the implanted medical device, sending the digital measurements and/or information to the processing system and employing the processing system to allow for internal offset calculation and account for the orientation change when the orientation sensing mechanism senses a change of orientation. In addition, or alternatively, the methods disclosed above may include monitoring the orientation of the electronic valve reader with the orientation sensing mechanism and alerting a clinician when the electronic valve reader orientation changes outside of a predetermined angular acceptance window so that the electronic valve reader can be reoriented before the reading process continues. In some embodiments, the alert or indication is provided prior to when the electronic valve reader would be out of attitude and need to be recalibrated.

BRIEF DESCRIPTION OF THE DRAWINGS

FIG. 1 is a perspective view of a subcutaneously implantable and adjustable fluid flow control device for use with an electronic valve reader.

FIG. 2 is a cross-sectional diagram further illustrating the subcutaneously implantable and adjustable fluid flow control device of FIG. 1.

DETAILED DESCRIPTION

Figure 3:
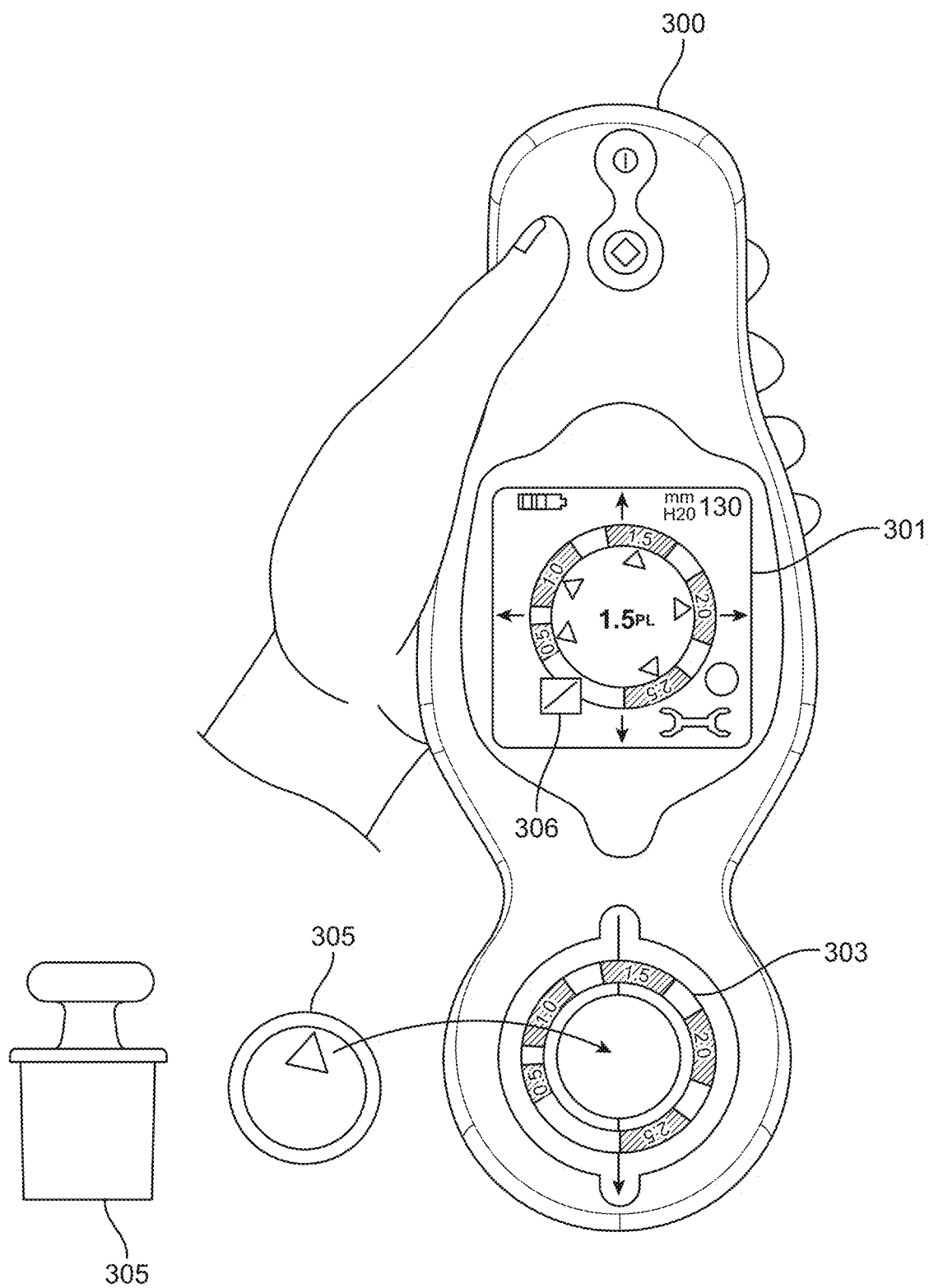
FIG. 3 is a schematic diagram illustrating an electronic valve reader and an adjustment tool.

FIGS. 1 and 2 illustrate one example of a subcutaneously implantable and percutaneously adjustable fluid flow control device 10. The fluid flow control device 10 is intended for use in a surgically implanted physiological shunt system for draining fluid from one portion of the body to another. In order to connect, for example, the flow control device 10 in such a system, the flow control device 10 includes an inlet connector 12 and an outlet connector 14 which each receive one end of a piece of surgical tubing (not shown). The ends of the surgical tubing are placed over the connectors 12 and 14 and secured thereon by a single ligature just inside of an annular ridge formed near the end of each connector 12, 14.

When the flow control device 10 is used in a drainage system intended for the treatment of hydrocephalus, the inlet connector 12 is fluidly connected with a proximal catheter that is inserted through the skull into a brain ventricle containing cerebrospinal fluid (CSF) under pressure. The outlet connector 14 is fluidly connected to a distal catheter (not shown) that serves to discharge cerebrospinal fluid to, for example, the atrium portion of a patient's heart. Ordinarily the flow control device 10 will be surgically implanted on the patient's skull with a flap of skin overlying the flow control device 10. To facilitate holding the flow control device 10 in its desired position after implantation, a generally flexible mounting plate can be provided with one or more suture holes.

The highly reliable fluid flow control device 10 has a single flow path 20 there through and a valve mechanism which can be percutaneously adjusted when the device 10 is subcutaneously implanted by the use of an electronic valve reader or "indicator tool" as disclosed herein and discussed in greater detail below. The flow control device 10 includes a relatively rigid, molded plastic base invested within an elastomeric casing 16 which, together, define the fluid flow path through the fluid flow control device 10 from the inlet connector 12 to the outlet connector 14. The valve housing includes a percutaneously adjustable valve mechanism that restricts the flow of fluid through the flow control device 10. Coupled to the adjustable valve mechanism is a magnetic indicator device that may be externally located using an electronic valve reader as described below. The flow control device is shown and described in more detail in U.S. Pat. No. 5,637,083 issued to Bertrand et al. entitled "Implantable Adjustable Fluid Flow Control Valve," the disclosure of which is hereby incorporated by reference.

Turning now also to FIG. 3, which is a diagram illustrating an example embodiment of a magnetic-based electronic valve reader 300. The electronic valve reader 300 of this embodiment includes a display module 301, a valve reader sensor module 303, and an adjustment tool 305. The valve reader sensor module 303 corresponds to magnetic sensor modules having respective magnetic sensor devices that electronically determine the location and orientation of a magnetic indicator device that is an integral part of a implanted flow control device, such as the fluid flow control device 10, which is discussed herein and fully disclosed in the '083 patent. The valve reader sensor module 303 uses a plurality of magnetic sensor devices, as discussed below and as disclosed in detail in the '668 and the '297 patents identified above. The valve reader sensor module 303 can further correspond to an orientation sensing mechanism including one or more acceleration sensor modules having at least one attitude sensor. A processing system including processing modules (not visible, see also, FIG. 6) within the valve reader sensor module 303 determine a corresponding valve setting for the adjustable control valve within the implanted flow control device based upon location and orientation of the magnetic indicator device and, in some embodiments, information received from an orientation sensing mechanism regarding changes in the orientation of the electronic valve reader during the reading process. In one embodiment, the valve reader sensor module 303 contains the magnetic sensor devices, attitude or acceleration sensors and some associated support electronics, while processing, display, power supply circuitry, and batteries may be contained inside the rest of the electronic valve reader 300.

From all of this information, the processing modules within the valve reader sensor modules 303 generate display data and information that is subsequently output to the display module 301 of the electronic valve reader 300 (see also, FIG. 6). In some embodiments, the display data represents a visual indication of the orientation of a valve control mechanism within the flow control device. The user of the electronic valve reader 300 may use this display data to determine whether the control valve within the flow control device 10 is set to a desired position.

In operation, the valve reader sensor module 303, and its plurality of magnetic sensor modules, are placed near the patient at a location in which the implanted flow control device is believed to be located. In many cases, a physician or other user may accurately identify this location for the flow control device and the valve reader sensor module 303 may be located on top of the implanted flow control device. During this reading process, the orientation sensing mechanism, having acceleration or attitude sensor modules, collects and provides digital measurements or other information to the processing modules relating to the x-y-zaxis orientation of the electronic valve reader (see also, FIG. 6). The electronics in the valve reader sensor module 303 process and detect electronic signals corresponding to magnetic fields generated by the magnetic indicator device that is part of the flow control device. These detected electronic signals may also correspond to magnetic fields associated with ambient and environmental sources. The effects on any applicable change in orientation detected from the orientation sensing mechanism and the effects from these ambient and environmental sources may be subtracted from the detected signals to determine a more accurate indication for the location and orientation of the magnetic indicator device that is part of the flow control device. The magnetic field data from each of the plurality of magnetic sensor modules permits a determination of the location and orientation of a magnetic indicator device to be expressed in five degrees of freedom: x, y, z, pitch, and yaw.

From this determined orientation of the magnetic indicator device that is part of the flow control device and from the known orientation of the flow control device, the processing modules may determine the present setting for the control valve within the flow control device. The processing required to translate the position of the magnetic indicator device to the setting of the control valve is easily determined in that the value corresponds to a rotatable wheel having a position within a circle of rotation for the magnetic indicator device that directly corresponds to the setting of the control valve within the flow control device. This translation processing is well understood and disclosed in detail within the '668 and '297 patents, referenced above, as the orientation of a compass within its circle of rotation directly corresponded to the setting for the control valve within the flow control device. Once the current position of the control valve is determined and displayed, the adjustment tool 305 may be used to alter the setting for the control valve within the flow control device, as will be discussed in greater detail below.

In certain embodiments, information and/or digital measurements received from the orientation sensing mechanism can be used by the processing system to provide an indication or alert 306 to a clinician if the orientation of the electronic valve reader 300 during the reading process has sufficiently varied either such that the orientation is at or outside of the predetermined angular acceptance window or threshold that is nearing the boundary of the predetermined angular acceptance window. The angular acceptance window or threshold can be set to be a change in orientation that is less than that which would result in the electronic valve reader 300 providing an error message that the control valve setting cannot be determined (i.e. the electronic valve reader is out of attitude range) and the reading process should be attempted again after recalibrating the electronic valve reader. In this way, the clinician is alerted that the electronic valve reader 300 should be re-orientated before the electronic valve reader 300 is out of attitude range. The indication or alert 306 can be visually provided on the display via the display module 301 or housing and/or the indication can also be audible, vibratory or the like.

Figure 4:
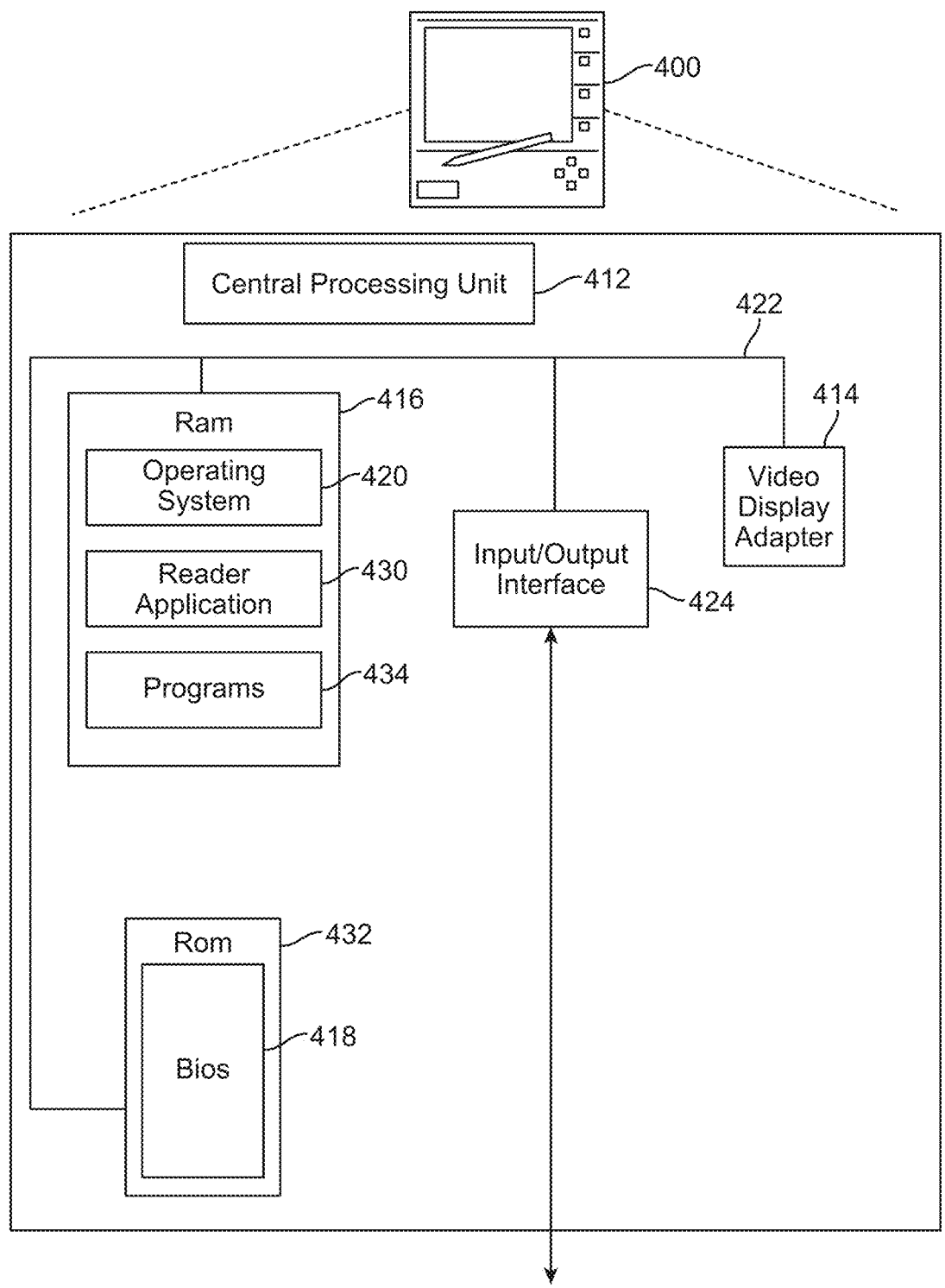
FIG. 4 is a block diagram illustrating a generally programmable processing system for use in a handheld device such as the electronic valve reader of FIG. 3.

Referring now also to FIG. 4, which is a block diagram generally illustrating the programmable processing system 400 for use in a handheld device, such as the electronic valve reader 300. In one embodiment of the magnetic valve reader processing system 400, the magnetic valve reader processing system 400 is operative to provide a magnetic valve indicator tool processing system. Those of ordinary skill in the art will appreciate that the magnetic valve reader processing system 400 may include many more components than those shown with reference to the magnetic valve reader processing system 400 shown in FIG. 4. However, the components shown are sufficient to disclose an illustrative embodiment for practicing the disclosed embodiments.

As shown in FIG. 4, the magnetic valve reader processing system 400 is used in connection with the implantable flow control device, such as the flow control device 10, as needed. The magnetic valve reader processing system 400 also includes one or more processing units 412, video display adapter 414, and a mass memory, all connected via bus 422. The mass memory generally includes RAM 416, ROM 432, and may include one or more mass storage devices, such as a removable memory device such as a Compact Flash, Smart Media, or Secure Digital memory card. The memory devices may store an operating system 420 for controlling the operation of magnetic valve reader processing system 400. It will be appreciated that this component may comprise a general purpose server operating system as is known to those of ordinary skill in the art, such as UNIX, MAC OS™, LINUX™, or Microsoft WINDOWS®. Basic input/output system ("BIOS") 418 is also provided for controlling the low-level operation of magnetic valve reader processing system 400.

The mass memory as described above illustrates another type of computer-readable media, namely computer storage media. Computer storage media may include volatile and nonvolatile, removable and non-removable media implemented in any method or technology for storage of information, such as computer readable instructions, data structures, program modules or other data. The mass memory also stores program code and data for providing a magnetic valve reader processing program. More specifically, the mass memory stores applications including magnetic valve reader processing program 430, and other programs 434, and similar analysis tool applications 436 as may be needed. The magnetic valve reader processing program 430 includes computer executable instructions which are executed to perform the logic described herein.

The magnetic valve reader processing system 400 also comprises input/output interface 424 for communicating with external devices, such as a touch screen and similar input devices, or other input devices not shown in FIG. 4. Likewise, the magnetic valve reader processing system 400 may further comprise additional mass storage facilities also not shown should additional data storage be needed.

One skilled in the art will recognize that the magnetic valve reader processing system 400 illustrated within FIG. 4 may represent a set of processing components typically found within a handheld or similar dedicated processing system. Of course, other processing systems including general purpose computing systems containing additional peripherals and user interface devices may also be used to implement the programmable processing according to various disclosed embodiments without deviating from the spirit and scope of the present disclosure.

FIG. 4 illustrates an example of a suitable operating environment in which the flow control device and electronic valve reader may be implemented. The operating environment is only one example of a suitable operating environment and is not intended to suggest any limitation as to the scope of use or functionality of the disclosed embodiments. Other well known computing systems, environments, and/or configurations that may be suitable for use with the disclosed embodiments include, but are not limited to, personal computers, server computers, hand-held or laptop devices, multiprocessor systems, microprocessor-based systems, programmable consumer electronics, network PCs, minicomputers, mainframe computers, distributed computing environments that include any of the above systems or devices, and the like. For example, a dedicated processing system may consist of a processor or digital signal processer (DSP) for performing the required floating-point math, various internal memory types including FLASH, ROM, RAM, and FPGA, some minimal external memory for the valve calibration system, and a user interface and display driver chip to run the switches and custom LCD or OLED display. A proprietary embedded operating system is and a specifically written application for implementing the reader program may be included.

The disclosed embodiments may also be described in the general context of computer-executable instructions, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Processing devices typically include at least some form of computer readable media. Computer readable media can be any available media that can be accessed by these devices. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by processing devices.

Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared, Bluetooth, and other wireless media. Combinations of any of the above should also be included within the scope of computer readable media.

Additionally, the embodiments described herein are implemented as logical operations performed by programmable processing devices. The logical operations of these various embodiments of the disclosed embodiments are implemented: (1) as a sequence of computer implemented steps or program modules running on a computing system; and/or (2) as interconnected machine modules or hardware logic within the computing system. The implementation is a matter of choice dependent on the performance requirements of the computing system implementing the present disclosures. Accordingly, the logical operations making up the embodiments of the disclosure described herein can be variously referred to as operations, steps, or modules.

Figure 5:
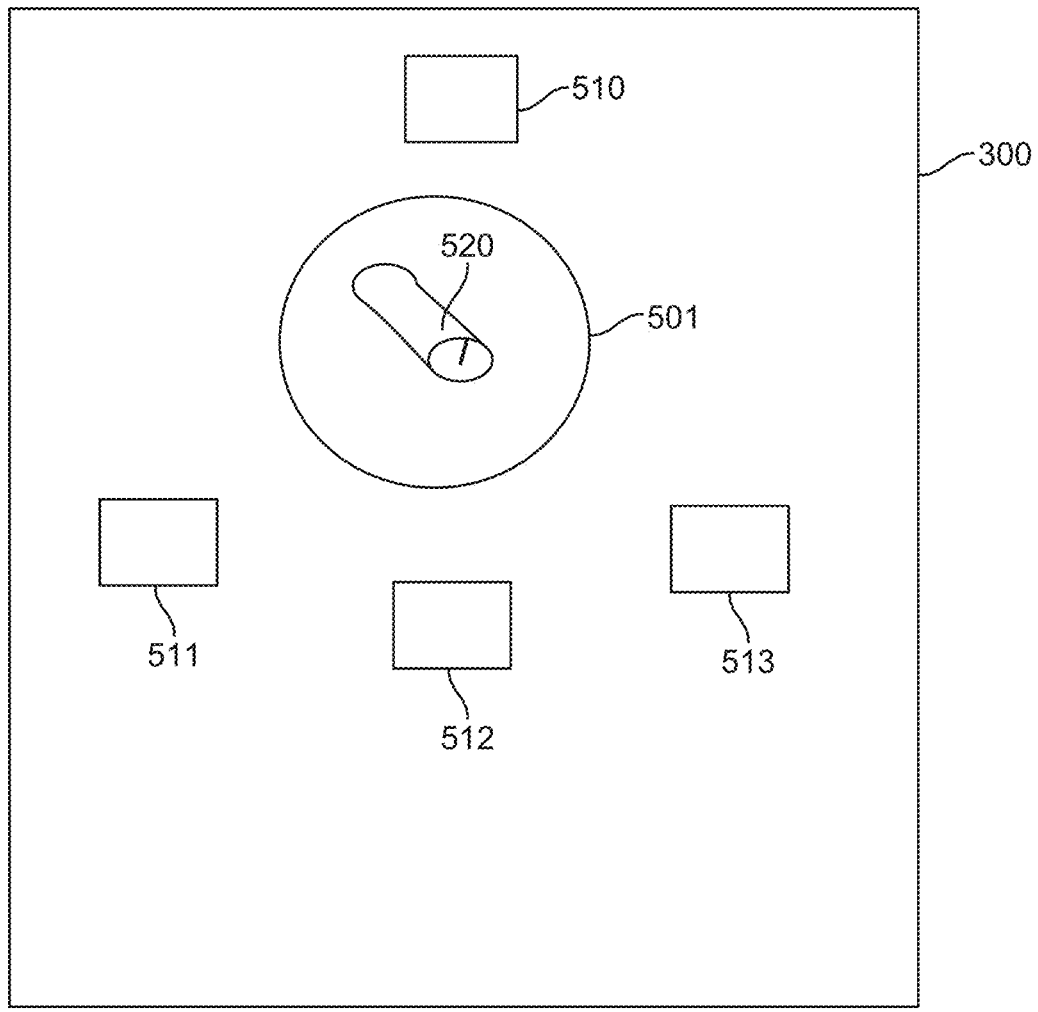
FIG. 5 is a block diagram illustrating a display showing a magnetic sensor device of the electronic valve reader of FIG. 3.

Turning now also to FIG. 5, which is a block diagram illustrating a magnetic device 520 within the electronic valve reader 300, in accordance with an example embodiment. The electronic valve reader 300 includes an opening 501 within the electronic valve reader 300 that permits the electronic valve reader 300 to be positioned over an implanted flow control device (e.g., the flow control device 10 described above with respect to FIGS. 1-2). The electronic valve reader 300 also includes a plurality of magnetic sensor devices 510-513 that each detect the magnetic field at their respective locations within electronic valve reader 300. The magnetic field detected by each magnetic sensor device 510-513 at its location is due to both background environmental magnetic fields and that arising from a magnetic device 520 located within the opening 501. As such, signals from the various magnetic sensor devices 510-513 may be processed to determine a location and orientation of the magnetic device 520 relative to the known positions of the magnetic sensor devices 510-513.

When the magnetic device 520 that is detected by the plurality of magnetic sensor devices 510-513 corresponds to a magnetic indicator device that is part of the valve within the flow control device 10, it is desired to determine the orientation of the magnetic indicator device relative to a known position of the flow control device in order to accurately determine the setting for the control valve within the flow control device. In one embodiment, the clinician orients the electronic valve reader 300 to a known orientation relative to the implanted flow control device (e.g., the flow control device 10). As such, the orientation of the magnetic indicator device 703, and thus the control valve, is determined relative to this known orientation. In other embodiments, additional measurements for additional position references may be used to perform this orientation and position translation operation. Because processing within the electronic valve reader 300 may be updated periodically or repeatedly, and may occur several times per second, ambient and environmental sources of magnetic fields may be estimated and subtracted from the observed signals generated by the plurality of magnetic sensor devices 510-513. These magnetic sensor devices 510-513 are generally located at dispersed locations about the electronic valve reader 300. In one embodiment, these magnetic sensor devices 510-513 may be located about one of the respective four corners of the electronic valve reader 300. Alternatively, a different number of magnetic sensor devices can be utilized (e.g., 3, 4, 5 and so on). Use of these magnetic sensor devices 510-513 in this fashion permits the electronic valve reader 300 to sense implanted magnetic devices at greater distances while being less sensitive to being centered coaxially over the implanted flow control device as compared to mechanical compass-based devices.

Figure 6:
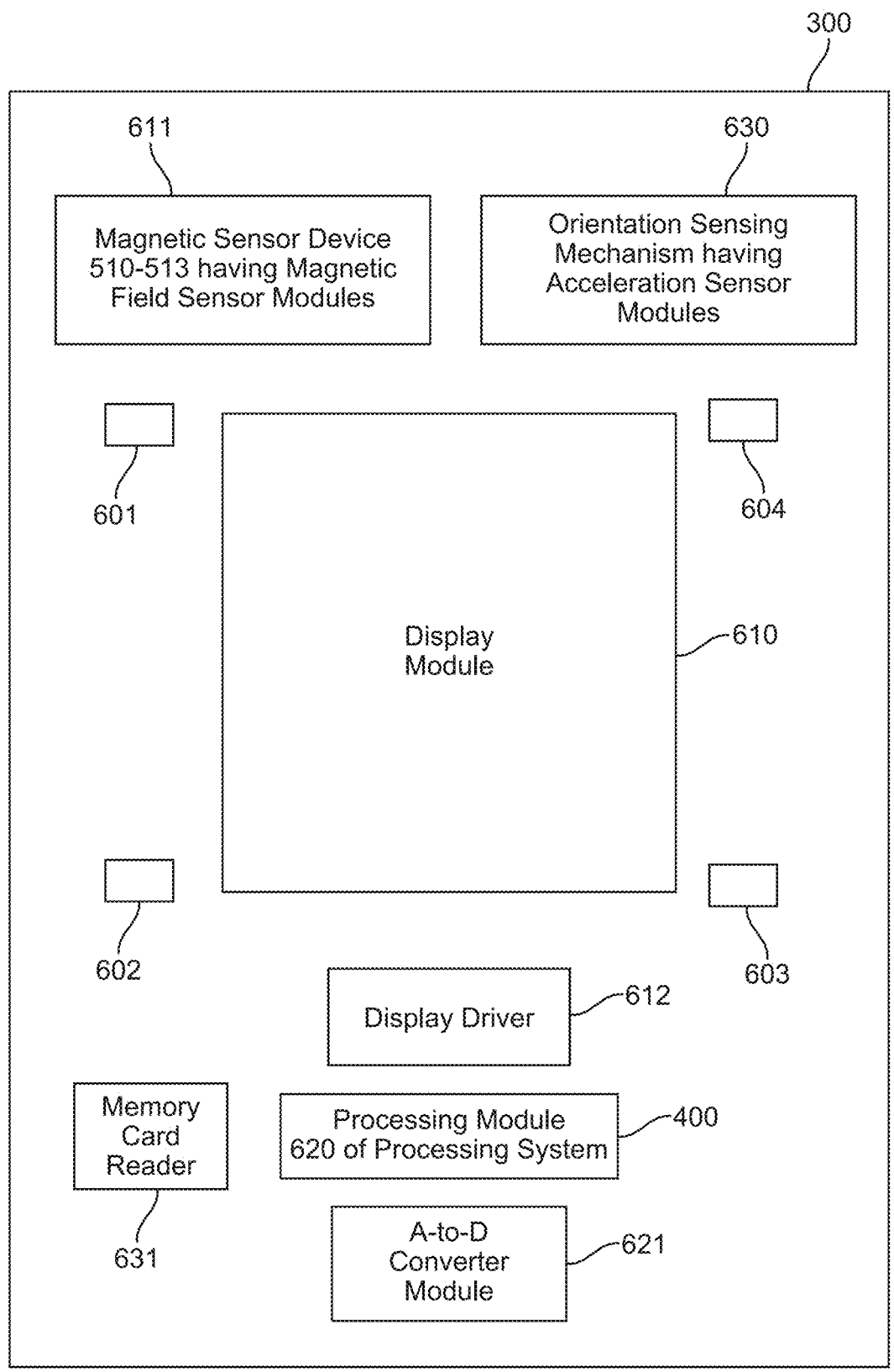
FIG. 6 is a block diagram illustrating internal components of the electronic valve reader of FIG. 3.

Referring now also to FIG. 6, which is a block diagram illustrating internal components of the electronic valve reader 300 including at least one processing module 620 that corresponds to a programmable processing system, such as the magnetic valve reader processing system 400 as discussed above with respect to FIG. 4. The electronic valve reader 300 is constructed using a display module 610 that is surrounded by a plurality of magnetic field sensor modules 601-604. Each of these four sets of magnetic field sensor modules 601-604 contain three separate sensors so as to measure the full, three-dimensional vector magnetic field detected by the module 601-604 at its location. The electronic valve reader 300 also contains the orientation sensing mechanism having one or more acceleration sensor modules 630, an analog-to-digital converter module 621 and a combined magnetic field sensor module 611 to electronically process the signals generated by the combined magnetic field sensor processing modules 601-604 to obtain digital measurements corresponding the observed magnetic field. These digital measurements of the observed magnetic field and, optionally, digital measurements obtained from the orientation sensing mechanism acceleration sensor modules 630 are subsequently processed within a processing module 620, which can be the same as that of FIG. 4 or could be a separate sub-processor, to determine the location and orientation of a magnetic indicator device within a field of view for the electronic valve reader 300. The processing module 620 performs operations upon the measured magnetic field data to determine the magnetic field generated by the magnetic indicator device while subtracting an estimate for ambient and environmental magnetic field also observed by the magnetic field sensor modules 601-604. The processing performed in this determination of the location and orientation of the magnetic indicator device, exclusive of adjustment based on digital measurements received from the acceleration sensor modules of the orientation sensing mechanism 630, is described in more detail within the '668 and the '297 patents to Haynor et al. discussed above. Examples, of suitable orientation sensing mechanisms include acceleration sensors include NXP-MMA7456L by NXP of Eindhoven, Netherlands, ST-LISDE12 by STMicroelectronics of Geneva, Switzerland.

As generally indicated in FIG. 6, the orientation sensing mechanism can alternatively have a gyroscope module, which includes attitude sensors. As also described above, the orientation sensing mechanism 630 can be configured to provide digital measurements to the magnetic valve reader processing system 620 regarding changes in orientation of the electronic valve reader 300 during the reading process. For example, changes in orientation can be monitored by the processing module 620 for the purpose of alerting the clinician to significant changes in orientation of the electronic valve reader 300. The digital measurements obtained from the orientation sensing mechanism 630 can also be accounted for by the processing module 620 when determining the location and orientation of the magnetic indicator device. An Example of a suitable orientation sensing mechanisms including gyroscopic sensors such as NXP-FXAS21002 by NXP of Eindhoven, Netherlands.

From the above location and orientation of the magnetic indicator device relative to the implantable flow control device (e.g., the implantable flow control device 10), the processing module 620 further determines the setting of the control valve. In certain embodiments, this setting data is then used to generate a display image and/or indication regarding orientation of the electronic valve reader 300 to be presented to a clinician on a display module 610. The processing module 620 can output the display and indication data to the display module 610 through a display driver 612.

Disclosed electronic valve readers (e.g., electronic valve reader 300) may further contain a memory card reader 631 for accepting computer readable storage media. In one embodiment, this storage media may include compact flash, start media, secure digital, and memory stick memory cards for providing the device replaceable memory containing data usable by the device. For example, an implantable flow control device (e.g., implantable flow control device 10) may permit fluid to flow at a particular pressure setting that corresponds to a particular setting on the control valve. When the electronic valve reader determines the control valve setting, the data from the memory card may be used to display the corresponding pressure setting. Because the valve-to-pressure setting may vary from particular models of implantable flow control devices, the use of a memory card corresponding to the model of the flow control device will permit the reader device to easily display pressure values for a wide variety of flow control devices without needing to maintain all of the valve-to-pressure setting data for all devices at one time.

Figure 7:
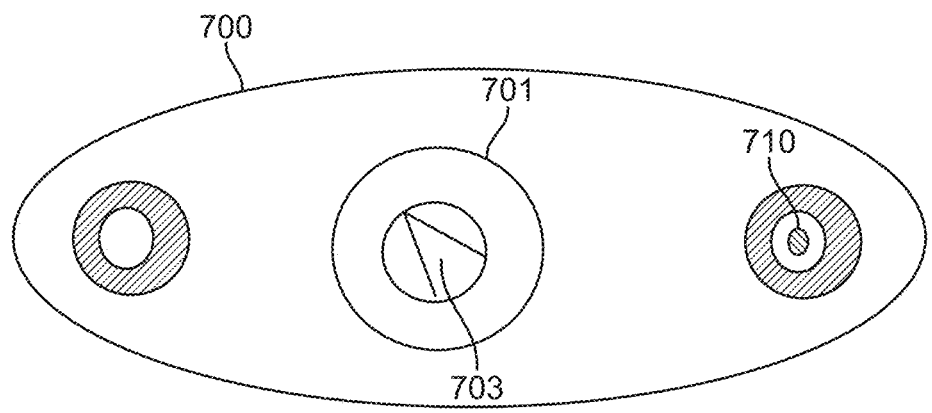
FIGS. 7 and 8 schematically illustrate alternate implantable valve devices possessing additional magnetic indicator devices for use with the electronic valve reader of FIG. 3.
Figure 8:
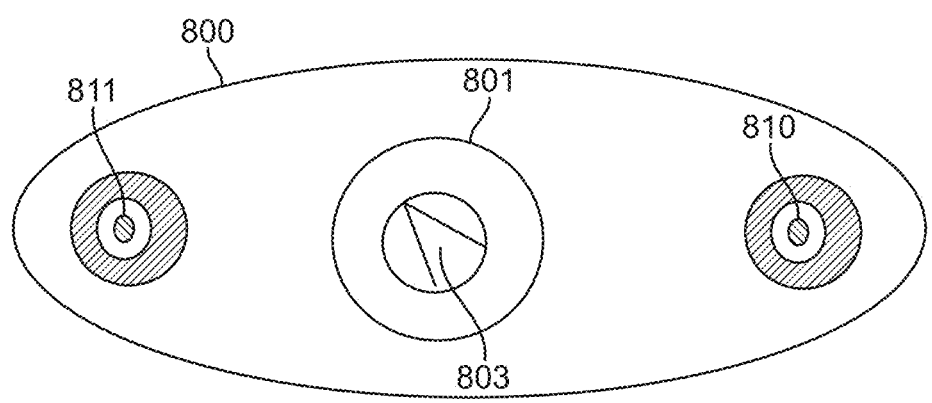

Referring now also to FIGS. 7 and 8, which schematically illustrate implantable valve devices possessing additional magnetic devices for use with the electronic valve readers disclosed herein. As discussed above, the location and orientation of a detected magnetic indicator device that is coupled to an implantable flow control device is used relative to an estimated position of the flow control device to determine the control valve setting. This estimate is made because the control valve is set by positioning the magnetic device coupled to the control valve such that as the control valve rotates about a known circular position, the magnetic field of the magnetic indicator device also rotates about the same circle. A user attempts to manually align the electronic valve reader into an orientation aligned with the implanted flow control device. As previously discussed, this alignment process can be difficult and it can also be challenging to maintain orientation of the electronic valve reader during the reading process. Therefore, the disclosed electronic valve readers include an orientation sensing mechanism to either sense and provide an offset calculation in view of sensed orientation measurements or alert a user of the electronic valve reader when electronic valve reader orientation is nearing or at an unacceptable variance or loss of orientation, as discussed above.

In an alternate embodiment, an additional magnet 710 is coupled to the implantable flow control device 700 in a location separate from the valve 701 and its magnetic indicator device 703. The electronic valve reader, such as the electronic valve reader 300, using the same processing to detect the magnetic device as discussed above, detects the location and orientation of the additional magnet 710. The location of the additional magnet 710 provides a reference point for the processing modules 620 within the electronic valve reader 300 to expressly determine the orientation of the electronic valve reader 300. The electronic valve reader 300 does not require the implanted flow control device 700 to be positioned into a known orientation relative to the electronic valve reader 300 in order to accurately determine the setting of the control valve 701. In this alternate embodiment, the setting of the control valve 701 may be made by determining the orientation of the magnetic indicator device 703 coupled to the control valve 701 relative to the position of the additional reference magnet 710. Using this method, the setting of the control valve 701 may be made accurately, yet independently of the orientation of the electronic valve reader 300 to the implanted flow control device.

In yet another embodiment, two separate reference magnets 810-811 are added to flow control device 800 so that the orientation of the control valve 801 and its corresponding magnetic indicator device 803 independently of the position of the electronic valve reader (e.g., the electronic valve reader 300). In alternate embodiments for the electronic valve reader, the electronic valve reader may utilize fewer magnetic sensor devices. The magnetic sensor devices provide information regarding the general orientation of the detected target and background magnetic fields. When the clinician orients the electronic valve reader in this embodiment to a desired orientation aligned with the implanted flow control device, the setting of the control valve 801 may be determined from the orientation of the magnetic fields observed from the magnetic indication device 803 coupled to the control valve 801 in addition to accounting for background fields, and, in some embodiments, changes in orientation of the electronic valve reader 300.

Figure 9:
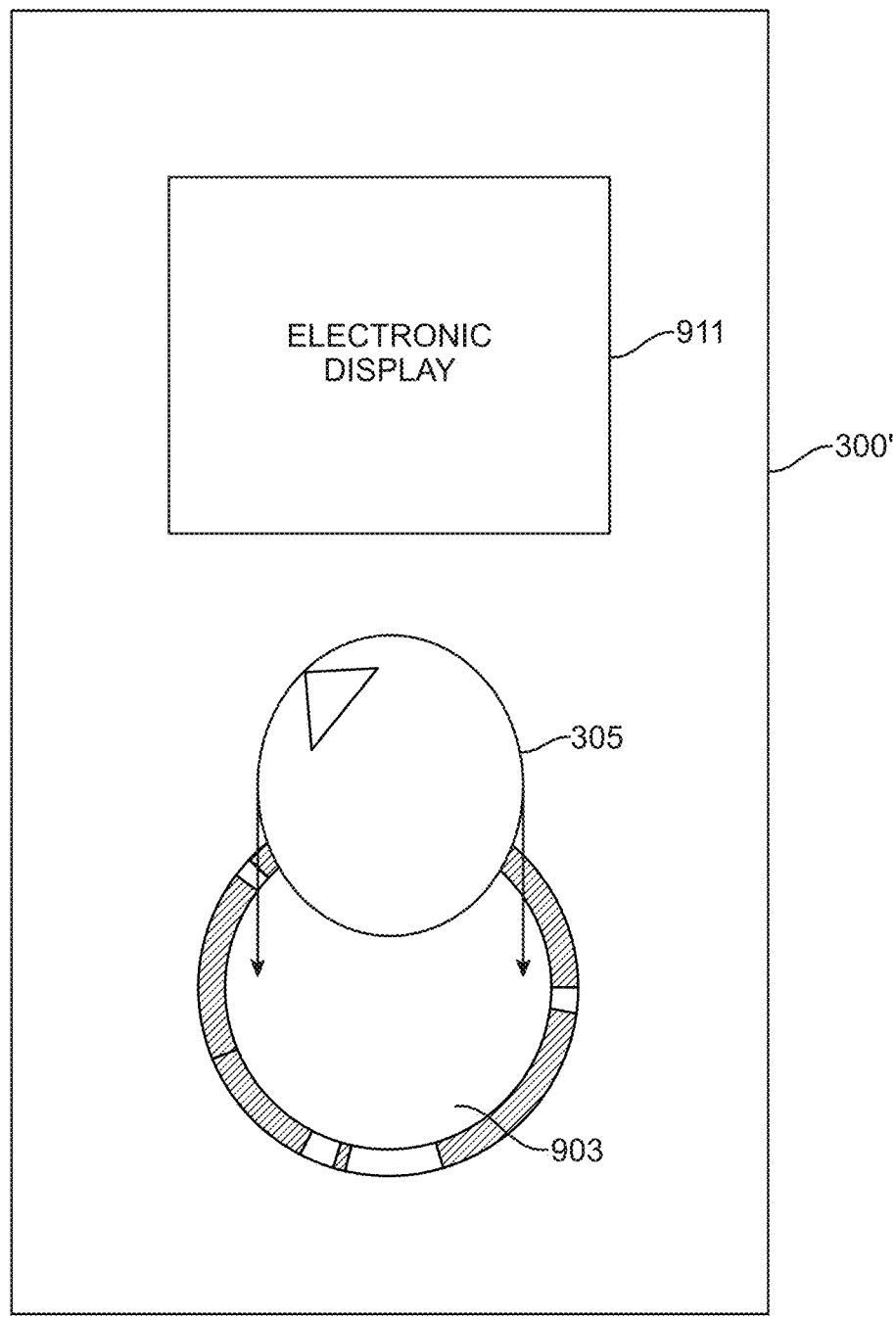
FIG. 9 is a diagram of the electronic valve reader of FIG. 3 in use with the adjustment tool as also shown in FIG. 3.

The electronic valve readers disclosed herein can include a display module 911 as generally depicted in FIG. 9, which illustrates a diagram of an alternate electronic valve reader 300' in accordance with an example embodiment. In this embodiment, the electronic valve reader 300 contains a display module 911 that displays the position of the control valve once the electronic valve reader 300' is positioned near an implanted flow control device. The process of determining the position of the control valve is discussed above in detail with respect to alternate embodiments. The display module 911 can further optionally display information provided from the processing system (e.g., the magnetic valve reader processing system 400) relating to changes in orientation of the electronic valve reader 300' based on changes sensed by the orientation sensing mechanism as discussed above with respect to the electronic valve reader 300 of FIG. 3. All other aspects of the electronic valve reader 300' can be configured and operate in accordance with alternate embodiments disclosed herein, as desired.

Once the current position of the valve is determined and displayed, the adjustment tool 305, which is identical to the adjustment tool 305 disclosed above, may be used to alter the setting for the control valve within the flow control device (e.g., the flow control device 10). The adjustment tool 305' corresponds to a magnetic coupling device that is placed over the valve reader sensor module 903 to orient the adjustment tool 905 directly over the magnetic indicator device that is part of the control valve. The adjustment tool 305 magnetically couples to the magnetic indicator device such that a rotation of the adjustment tool 305 within its location above the valve reader sensor module 903 causes the magnetic indicator device to rotate within the control valve. This rotation of the magnetic indicator device changes the settings for the control valve within the flow control device as the magnetic indicator device is directly coupled to the valve adjustment mechanism or tool 305. The operation of the adjustment tool 305 is disclosed in additional detail in U.S. Patent to Bertrand et al., U.S. Pat. No.

8,622,978, the disclosure of which is incorporated herein in its entirety. These modules operate together as disclosed herein to provide the operation of an electronic valve reader and a valve adjustment tool.

Figure 10:
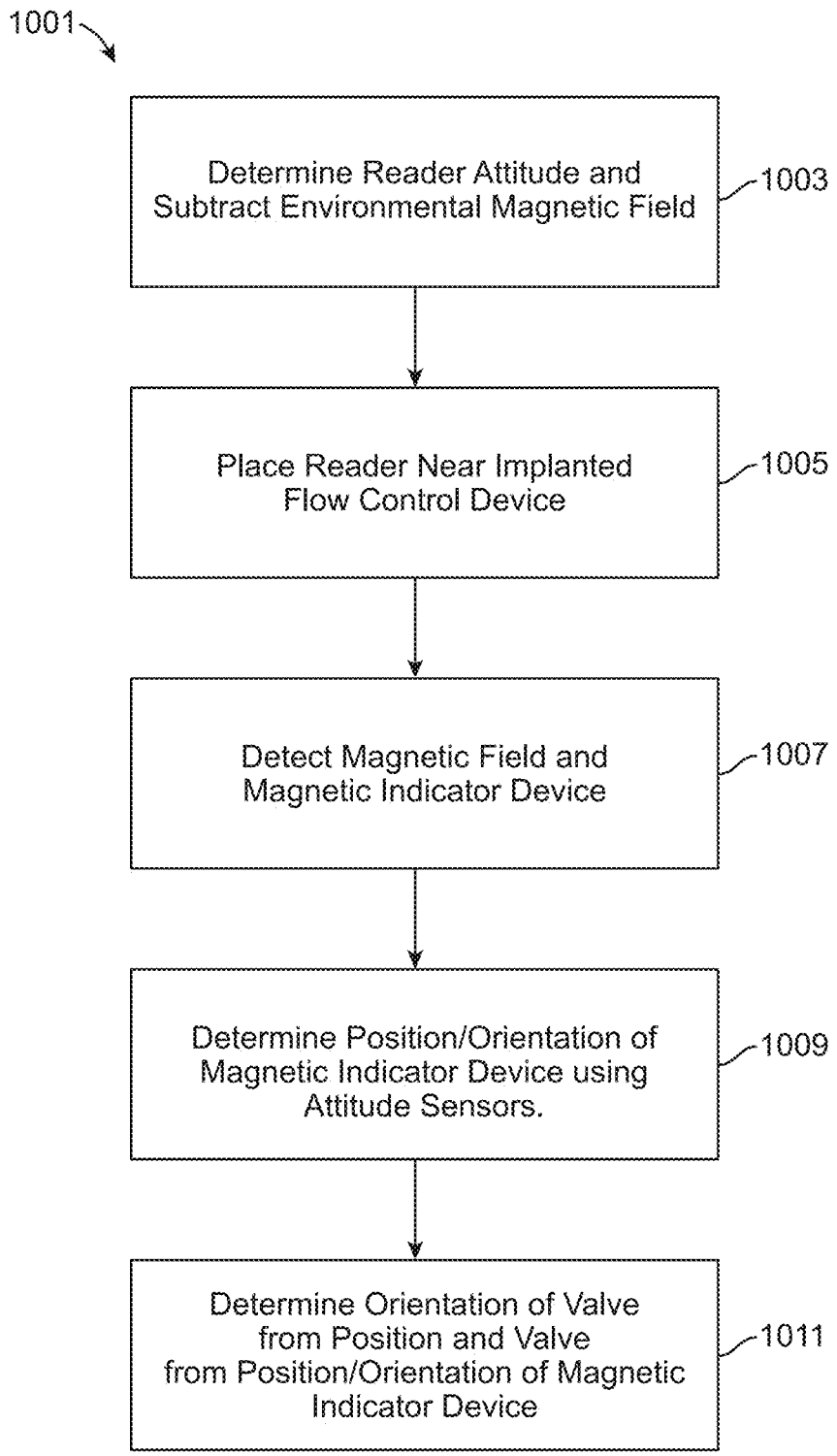
FIG. 10 is a flowchart of one exemplary method of using the electronic valve reader of FIG. 3.

Turning now also to FIG. 10, which generally illustrates a reading process 1001 or method of determining the setting of a control valve of an implantable flow control device, such as the implantable flow control device 10, with the electronic valve readers disclosed herein in accordance with an example embodiment. The method begins by determining an estimate for background magnetic fields and electronic valve reader attitude 1003. The estimate for a background magnetic fields value is determined by obtaining a set of magnetic field values that are averaged to obtain this estimate for the background fields from environmental and ambient sources. The attitude of the electronic valve reader is determined with the orientation sensing mechanism. Next, the method continues by placing the electronic valve reader near the implantable flow control device 1005 within a patient to detect a target magnetic field of a magnetic indicator device 1007 of the implantable flow control device. Because the target magnetic field typically observable at a distance of 12 cm from a typical magnetic indicator device coupled to an implantable flow control device is generally less than 5 milliGauss, the electronic valve reader must be positioned as close as possible to the flow control device to permit the electronic valve reader to detect this magnetic field within the Earth's background magnetic field, which is typically observed to be approximately 500 milliGauss. During this placement, it is possible that the orientation of the electronic valve reader may be lost or vary significantly. The orientation sensing mechanism and its attitude sensors provide digital measurements regarding the changes in orientation of the electronic valve reader to the processing module to allow for internal offset calculation of an orientation change of the electronic valve reader, as discussed above.

Once the electronic valve reader is located as close to the flow control device as possible, the electronic valve reader detects an observed magnetic field from all sources 1007 (i.e. target and background sources). The background magnetic fields estimate 1003 is subtracted from the observed magnetic field values 1007 to obtain a position and orientation for the magnetic indicator device 1009 coupled to the control valve that is part of the implanted flow control device. In some embodiments, the detected magnetic field and processed position and orientation for the magnetic indicator device are repeated at a rate of several times per second. As discussed above, digital measurements relating to a change in orientation of the electronic valve reader can also be used to determine the position and orientation for the magnetic indicator device 1009.

The position or orientation of the magnetic indicator device is compared to a known orientation of the flow control device to determine a setting/orientation for the control valve of the flow control device 1011. The known orientation of the flow control device may be manually determined by requiring the electronic valve reader to be oriented to a particular position relative to flow control. The known orientation of the flow control device may also be determined from a detection of other reference positions, such as a separate reference magnet (i.e. magnetic indicator device) as discussed above. Once the electronic valve reader has determined the setting for the control valve, a user may utilize an adjustment tool to magnetically rotate and thus alter the setting/orientation of the valve, as desired.

Figure 11A:
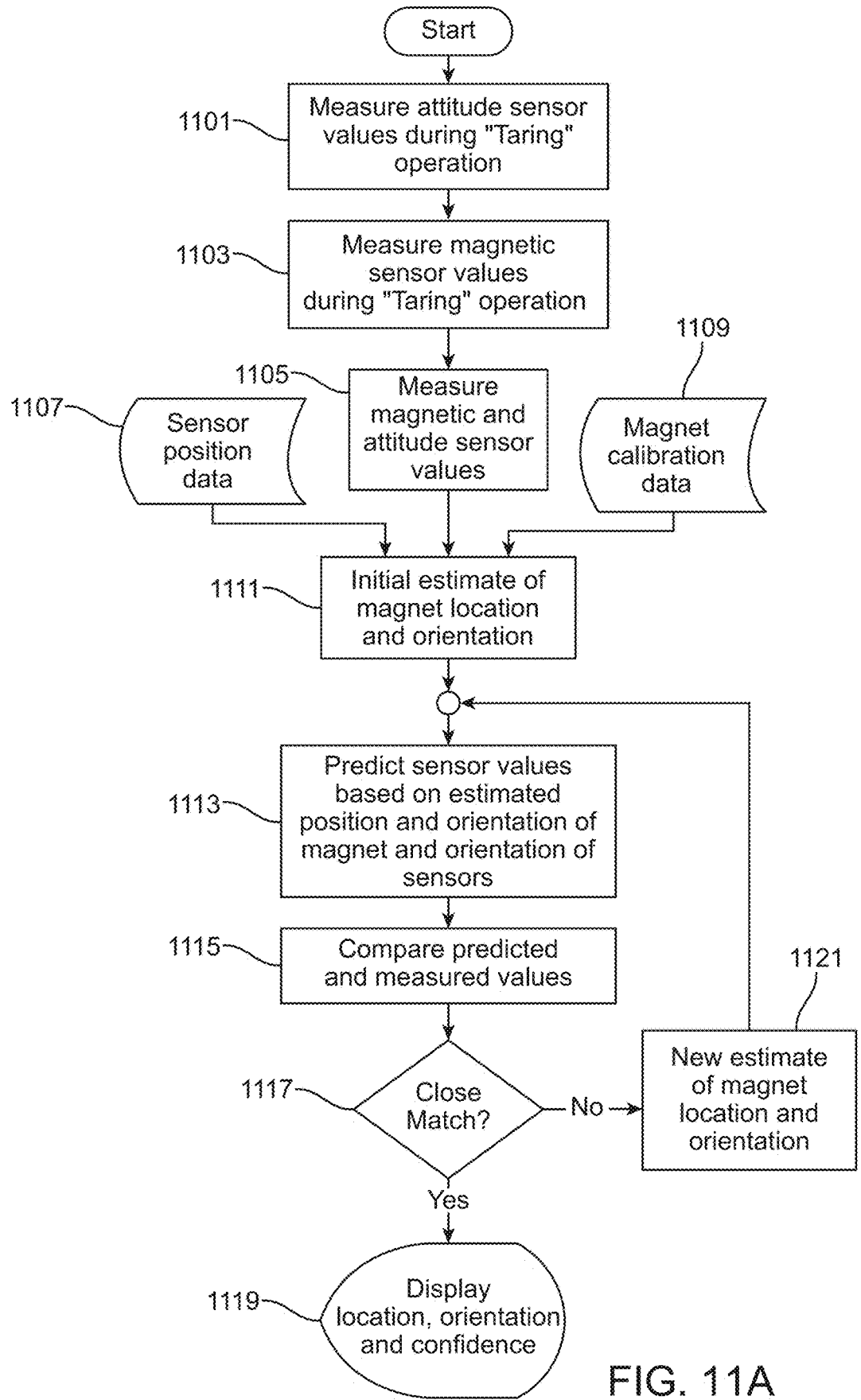
FIG. 11A is a flowchart of the operation of one example of an electronic valve reader.

Referring now also to FIG. 11A, which is a flowchart generally illustrating the operation of an electronic valve reader, such as those disclosed above, in accordance with an example embodiment in which the orientation sensing mechanism is used to account for changes in the orientation of the electronic valve reader during the reading process when determining an implantable medical device setting. First, the electronic valve reader measures the attitude sensor values and magnetic sensor values for conducting a zero setting or taring operation 1101-1103 to account for background magnetic fields 1103 and to establish an initial position of the electronic valve reader with the attitude sensor position data or other digital measurements 1107. Steps 1101 and 1103 can occur simultaneously or in reverse order. The magnet calibration data 1109 is determined by obtaining a set of magnetic field values that are averaged to obtain this estimate for the background fields from environmental and ambient sources. The magnetic field values 1109 are sent to the processing system to prepare an initial estimate of the magnet/target location and orientation 1111. Next, the processing system predicts magnetic sensor values 1113 based on an estimated position and orientation of the magnet/target and orientation of the magnetic sensors. The predicted and measured values are then compared to each other 1115. If the predicted and measured valves are a close match 1117, the location and orientation of the magnetic indicator device is displayed for the clinician, optionally along with confidence information 1119. If the predicted and measured values are not a close match, a new estimate of the magnet location and orientation is prepared 1121 by repeating steps 1113-1117 until a close match is obtained. The threshold for what is considered a "close match" can vary, as desired. For example, the electronic valve reader 300 can be set to various levels of tolerance (e.g., 0.5, 1.0, 1.5, 2.0 or 2.5) as can be seen in FIG. 3.

Figure 11B:
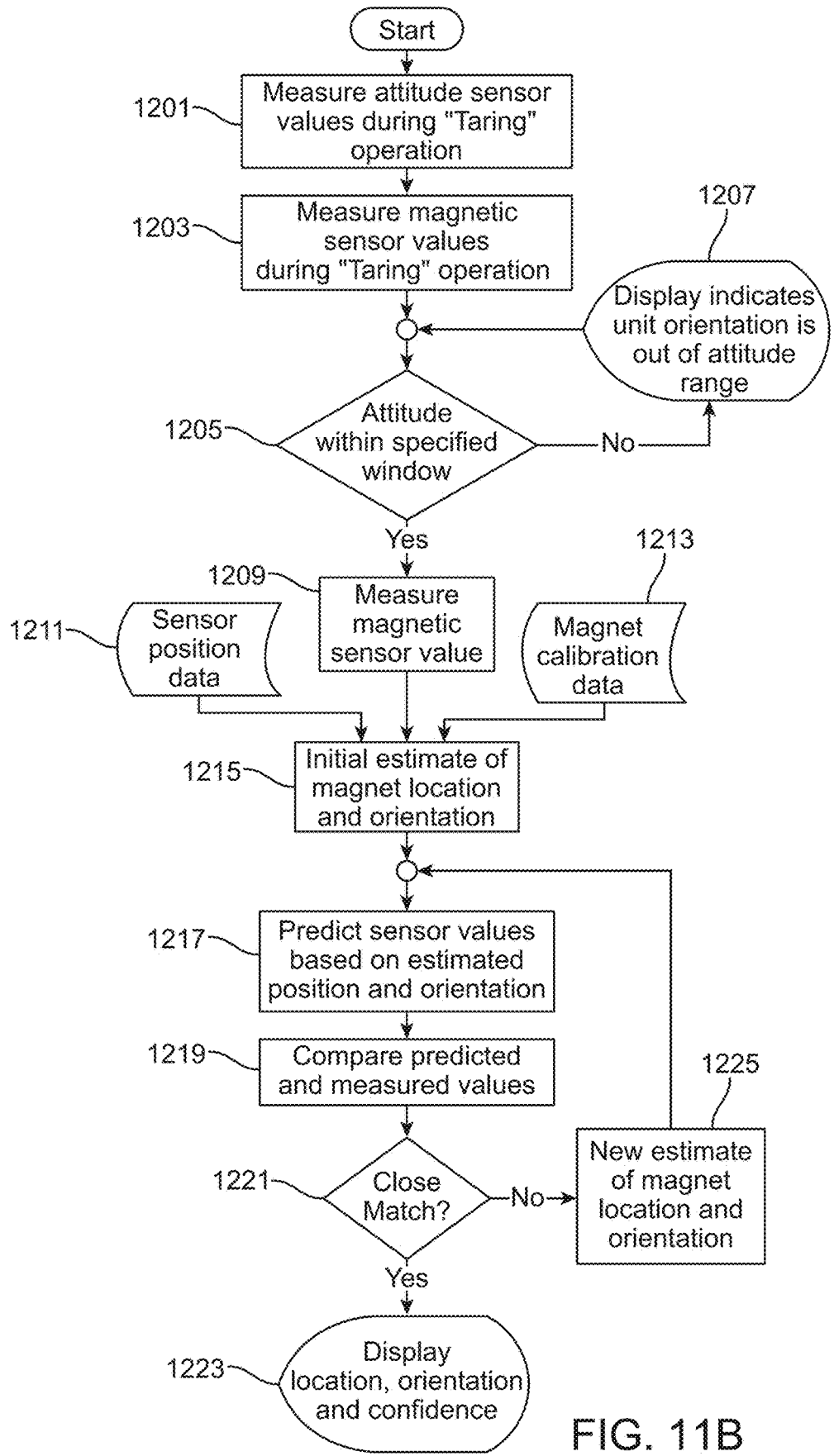
FIG. 11B is a flowchart of the operation of another example of an electronic valve reader.

Referring also now to FIG. 11B, which is a flowchart generally illustrating the operation of an electronic valve reader, such as those disclosed above, in accordance with an alternate example embodiment in which the orientation sensing mechanism is used to monitor the orientation of the electronic valve reader so that a clinician can be alerted if the orientation is varied significantly. Similar to the previous embodiment, the electronic valve first reader measures the attitude sensor values and magnetic sensor device values for conducting a zero setting or taring operation 1201-1203 to account for background magnetic fields and to establish an initial position of the electronic valve reader with sensor position data or measurements. Then, as the electronic valve reader is moved toward the implantable medical device, the attitude sensor values are monitored by the processing system. If the attitude or change in orientation is either at or falls outside of a specified window 1205, an indication is provided to the user (e.g., on the display) that the orientation is out of range or outside of the window 1207. If the orientation or attitude remains within the predetermined window, the magnetic sensor value is measured 1209 and, along with the sensor positon of the magnetic indicator device and magnet calibration data 1211-1213, is used to prepare an initial estimate of the magnet/target location and orientation 1215 of the magnetic indicator device. Next, the processing system predicts the magnetic sensor values 1217 based on an estimated position and orientation of the magnet/target and orientation of the magnetic sensors. The predicted and measured values are compared to each other 1219. If the predicted and measured valves are a close match as determined at step 1221, the magnetic sensor location and orientation is displayed for the clinician 1223, optionally along with confidence information. If the predicted and measured values are not a close match as determined at step 1221, a new estimate of the magnetic indicator device location and orientation is prepared 1225 by repeating steps 1217-1221 until a close match is obtained. The threshold for what is considered a "close match" can vary, as desired. For example, the electronic valve reader 300 can be set to various levels of tolerance (e.g., 0.5, 1.0, 1.5, 2.0 or 2.5) as can be seen in FIG. 3.

Although the present disclosure has been described with reference to preferred embodiments, workers skilled in the art will recognize that changes can be made in form and detail without departing from the spirit and scope of the present disclosure.

What is claimed is:

1. A magnetic-based electronic valve reader for determining a setting of an implantable medical device having a control valve and a magnetic indicator device, the magnetic-based electronic valve reader comprising:
   a housing having a display;
   a plurality of magnetic sensor devices for use in determining a spatial location and orientation of the magnetic indicator device of the implantable medical device;
   an orientation sensing mechanism within the housing that measures an oriententation or changes in the orientation of the housing; and
   a processing system including at least one processing module that receives magnetic sensor values from the plurality of magnetic sensor devices and determines a sensor value related to the control valve of the implantable medical device when the housing is at a predetermined orientation range.

2. The magnetic-based electronic valve reader of claim 1, wherein the orientation sensing mechanism is selected from the group consisting of a gyroscope and an accelerometer.

3. The magnetic-based electronic valve reader of claim 1, wherein the processing system is configured to generate a signal to provide an indication of the electronic valve reader to the change in orientation of the housing that is either at or outside of a predetermined angular acceptance window.

4. The magnetic-based electronic valve reader of claim 3, wherein the predetermined angular acceptance window is set to generate the signal before the electronic valve reader will need to be recalibrated in order to determine the implantable medical device setting.

5. The magnetic-based electronic valve reader of claim 3, wherein the indication is provided on the display.

6. The magnetic-based electronic valve reader of claim 3, wherein the processing system is configured to utilize digital measurements received from the orientation sensing mechanism regarding the orientation of the housing to determine the setting for the control valve.

7. The magnetic-based electronic valve reader of claim 1, wherein the processing system is configured to utilize digital measurements received from the orientation sensing mechanism regarding the orientation of the housing to determine the setting for the control valve.

8. The magnetic-based electronic valve reader of claim 7, wherein the digital measurements relate to changes in a spatial orientation of the electronic valve reader.

9. The magnetic-based electronic valve reader of claim 1, wherein the at least one processing module that receives digital measurements from the orientation sensing mechanism and determines a sensor value for the implantable medical device based on both the magnetic sensor values and the digital measurements.

10. A method comprising:
    providing an implanted medical device having a magnetic indicator device coupled to a control valve used to control operation of the implantable medical device;
    providing a magnetic-based electronic valve reader having a plurality of magnetic sensor devices for use in determining a spatial location and orientation of the magnetic indicator device and an orientation sensing mechanism that is separate from the plurality of magnetic sensor devices;
    conducting a taring operation regarding the orientation of the electronic valve reader in three-dimensional space;
    placing the electronic valve reader adjacent to the implantable medical device;
    measuring changes in the orientation of the electronic valve reader in three dimensional space with the orientation sensing mechanism; and
    measuring a magnetic field strength observed by the electronic valve reader with the plurality of magnetic sensor devices to allow a determination of a control valve setting.

11. The method of claim 10, wherein the electronic valve reader includes a processing system; the method further comprising the step of sending digital measurements obtained from the orientation sensing mechanism to the processing system and the step of using the digital measurements in the determination of the control valve setting; wherein the digital measurements relate to changes in three-dimensional orientation of the electronic valve reader as the electronic valve reader is placed adjacent the implantable medical device.

12. The method of claim 10, wherein the method further includes the step of detecting a change in orientation of the electronic valve reader is either at or outside a predetermined angular acceptance window with the orientation sensing mechanism.

13. The method of claim 12, the method further comprising the step of providing an indication that the orientation of the electronic valve reader is at or outside of the predetermined angular acceptance window.

14. The method of claim 12, wherein the predetermined angular acceptance window is configured such that the indication is provided before the electronic valve reader will need to be recalibrated in order to determine the device setting.

15. The method of claim 12, wherein the indication is provided on a display of the electronic valve reader.

16. The method of claim 15, further comprising the step of reorienting and recalibrating the electronic valve reader after the indication is provided.

17. The method of claim 12, wherein the electronic valve reader includes a processing system; the method further comprising the step of sending digital measurements obtained from the orientation sensing mechanism to the processing system and the step of using the digital measurements to determine the control valve setting.

18. The method of claim 10, wherein the orientation sensing mechanism is selected from the group consisting of a gyroscope and an accelerometer.

19. The method of claim 10, wherein the step of determining occurs repeatedly throughout the step of placing the electronic valve reader.

20. A magnetic-based electronic valve reader for determining a setting of a control valve of an implantable medical device having a magnetic indicator device associated with the control valve, the magnetic-based electronic valve reader comprising:

a housing;

a plurality of magnetic sensor devices within the housing for use in determining a spatial location and orientation of the magnetic indicator device;

an orientation sensing sensor within the housing that senses and measures an orientation or changes in the orientation of the housing; and a processing system including at least one processing module to determine a setting of the control valve of the implantable medical device based on both (1) received magnetic sensor values from the plurality of magnetic sensor devices and (2) received digital measurements from the orientation sensing sensor.

\* \* \* \* \*

UNITED STATES PATENT AND TRADEMARK OFFICE
CERTIFICATE OF CORRECTION

| | |
|---|---|
| PATENT NO. | : 12,121,685 B2 |
| APPLICATION NO. | : 18/345265 |
| DATED | : October 22, 2024 |
| INVENTOR(S) | : Drew Amery |

It is certified that error appears in the above-identified patent and that said Letters Patent is hereby corrected as shown below:

On the Title Page

Page 2, Column 2, item [56], Other Publications, Line 9, Before "International", delete "A"

In the Specification

Column 6, Detailed Descriptions, Line 28, Delete "x-y-zaxis" and insert --x-y-z-axis-- therefor Column 14, Detailed Descriptions, Line 57, Delete "positon" and insert --position-- therefor In the Claims Column 15, Line 26, In Claim 1, Delete "orientention" and insert --orientation-- therefor Signed and Sealed this
Sixth Day of May, 2025

Coke Morgan Stewart
*Acting Director of the United States Patent and Trademark Office*